United States Patent
Mogi

[11] Patent Number: 5,873,838
[45] Date of Patent: Feb. 23, 1999

[54] SENSITIVITY SETTING DEVICES AND ELECTROCARDIOGRAPHS INCLUDING THE SENSITIVITY SETTING DEVICES

[75] Inventor: Tomohiro Mogi, Koganei, Japan

[73] Assignee: Casio Computer Co., Ltd., Tokyo, Japan

[21] Appl. No.: 833,578

[22] Filed: Apr. 7, 1997

[30] Foreign Application Priority Data

Apr. 26, 1996 [JP] Japan ................................. 8-106758

[51] Int. Cl.$^6$ ................................. A61B 5/0402
[52] U.S. Cl. ................................. 600/509; 128/901
[58] Field of Search ................... 128/696, 901, 128/902

[56] References Cited

U.S. PATENT DOCUMENTS 3,927,663 12/1975 Russell et al. .......................... 128/901
4,606,352  8/1986 Geddes et al. .

*Primary Examiner*—Scott M. Getzow
*Attorney, Agent, or Firm*—Frishauf, Holtz, Goodman, Langer & Chick

[57] ABSTRACT

A sensitivity setting device and an electrocardiograph which includes the sensitivity setting device include a differential amplifier whose amplification factor is changed by a CPU and a CR differentiator connected to the differential amplifier for providing an appropriate electrocardiogram waveform. The CR differentiator includes capacitor and two parallel resistors connected with the capacitor with one of the resistors being connected to an analog switch which is switched on/off by the CPU. If there is an input electrocardiogram waveform from a pair of electrodes attached to a patient's body directly after the measurement of the electrocardiogram waveform, the electrocardiogram waveform is amplified with an initial set amplification factor by the differential amplifier and the resulting signal is inputted to the CR differentiator. When the analog switch is switched on to reduce the CR time constant of the CR differentiator, an accurate electrocardiogram waveform is picked up and an appropriate sensitivity is obtained from the amplitude of the picked-up electrocardiogram waveform. A corresponding amplification factor is then set in differential amplifier, the analog switch is switched off, and the electrocardiogram waveform is measured with the appropriate time constant.

7 Claims, 3 Drawing Sheets

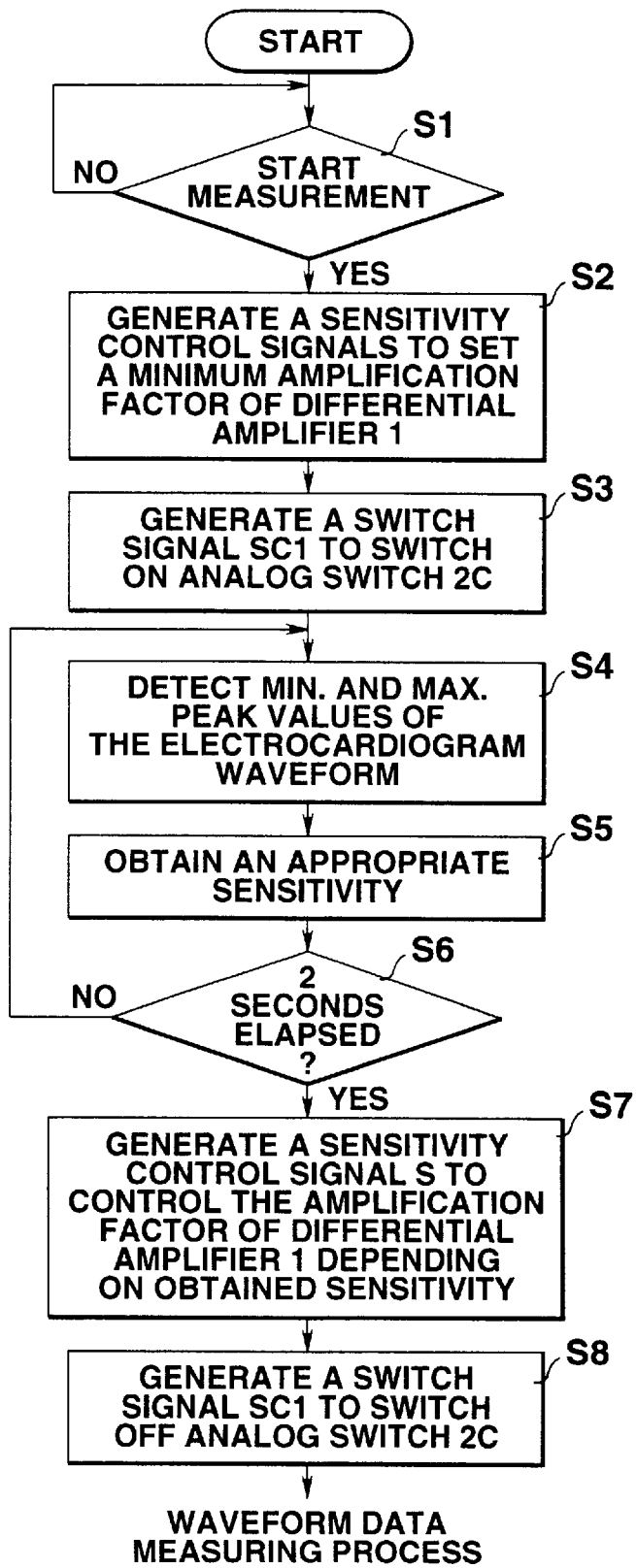

SENSITIVITY SETTING DEVICES AND ELECTROCARDIOGRAPHS INCLUDING THE SENSITIVITY SETTING DEVICES

BACKGROUND OF THE INVENTION

1. Field of the Invention

The present invention relates to electrocardiographs, and more particularly to a sensitivity setting device which automatically sets an appropriate sensitivity in a device which senses a faint living body signal, and an electrocardiograph which includes such sensitivity setting device.

2. Description of the Related Art

Conventionally, an electrocardiograph used for diagnosis of heart diseases such as irregular pulses and/or myocardial infraction is known. The electrocardiograph picks up a faint voltage produced each time a myocardium shrinks from electrodes stuck with a paste, for example, on a patient's breast, amplifies the voltage, and records it as an electrocardiogram waveform (or electrocardiogram).

The maximum voltage level of the electrocardiogram waveform measured by the electrocardiograph varies from several hundreds of microvolts to several scores of millivolts depending on the patient or the manner in which the electrodes are attached to the patient. Thus, in measurement, the sensitivity (amplification factor) is required to be adjusted so as to provide an optimal dynamic range.

To this end, recently, electrocardiographs which include a sensitivity setting device which automatically sets sensitivity to provide an optimal dynamic range have been put to practical use. If the sensitivity is switched during recording of the electrocardiogram waveform, the electrocardiogram provided for diagnosing purposes becomes difficult to view. Thus, in the electrocardiograph of this type, a sensitivity determining period prior to starting the recording of the electrocardiogram waveform is provided to thereby set an optimal sensitivity for measurement of the electrocardiogram waveform during the sensitivity determining period.

However, in such conventional sensitivity setting device, the following problems arise. It is known that the electrocardiogram waveform greatly sways due to fluctuations of a reference potential level called a baseline fluctuation BD, as shown in FIG. 2B, in the initial state of the electrocardiogram investigation directly after the electrodes are set when the contact between the electrodes and the patient's skin is not electrically stable.

When the baseline fluctuation BD occurs in the sensitivity determining period where the automatic sensitivity is set, the difference between the maximum and minimum waveform values of the electrocardiogram waveform is large, and the sensitivity is conventionally automatically set to provide a dynamic range conforming to the difference. Hence the sensitivity for the electrocardiogram waveform in this situation becomes very low.

Thus, the electrocardiogram waveform conventionally recorded in the above described situation is very small and not suitable for diagnosis. Even in a digital sampling-type electrocardiograph, resolution becomes coarse in the sampling and only an, electrocardiogram waveform having a low resolution is obtained even when enlarged and displayed.

Accordingly, a sensitivity setting device has been long awaited which is capable of measuring with an optimal sensitivity a small signal superimposed on a reference voltage without being influenced by possible fluctuations of the reference voltage (baseline).

SUMMARY OF THE INVENTION

It is therefore an object of the present invention to provide a sensitivity setting device which is capable of setting an optimal sensitivity by removing the influence of fluctuations of a reference voltage, and an electrocardiograph which includes such sensitivity setting device.

In order to achieve the above object, according to the present invention, there is provided a sensitivity setting device for changing a measurement sensitivity to an optimal one as required and for measuring an inputted electrocardiogram waveform with the optimal sensitivity, comprising:

measurement starting means for starting the measurement of the electrocardiogram waveform;

filter means for filtering out possible noise from the electrocardiogram waveform with a predetermined time constant;

time constant setting means responsive to the starting of the measurement of the electrocardiogram waveform by the measurement starting means for setting the time constant of the filter means at a value smaller than the predetermined time constant;

amplitude detecting means for detecting the amplitude of the electrocardiogram waveform, from which the possible noise is filtered out, with the time constant set by the time constant setting means; and sensitivity setting means for setting the measurement sensitivity at such a value that the amplitude detected by the amplitude detecting means falls within a predetermined range.

By such arrangement, an optimal sensitivity is set automatically in a device which senses a faint living body signal.

BRIEF DESCRIPTION OF THE DRAWINGS

FIG. 3 is a flow chart indicative of the operation of a portable electrocardiograph of the embodiment 2.

DESCRIPTION OF THE PREFERRED EMBODIMENTS

A sensitivity setting device according to the present invention applies to devices such as electrocardiographs and electroencephalographs which measure living body signals as well as measuring devices which handle a faint signal superimposed on the reference voltage. Next, a portable electrocardiograph as an embodiment of the present invention will be described with reference to the accompanying drawings.

A. Structures of First and Second Embodiments

In circuit composition, the first and second embodiments are the same and will be described together.

Figure 1:
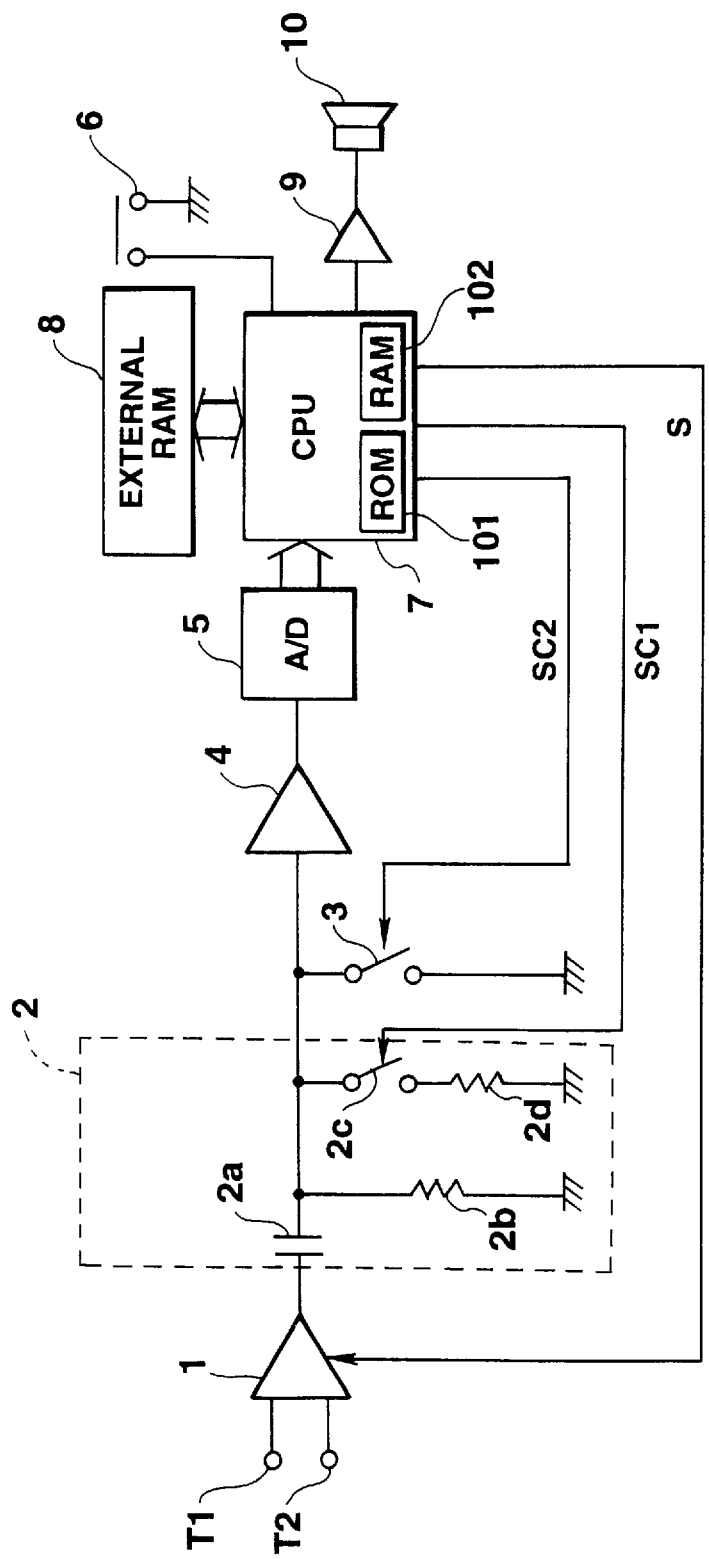
FIG. 1 is a block diagram of embodiments 1 and 2 of the present invention.

FIG. 1 is a block diagram of a portable electrocardiogram as the embodiment of the present invention. In FIG. 1, a pair of electrodes Ti, T2 are applied to measuring positions on a patient's body to pick up a faint voltage produced each time the myocardium shrinks. A differential amplifier 1 comprising an operational amplifier eliminates common mode noise produced across the electrodes T1 and T2 and outputs an electrocardiogram waveform corresponding to the voltage difference across the electrodes T1 and T2. The differential amplifier 1 is arranged so that its amplification factor is controlled depending on a sensitivity control signal S fed from a CPU 7 to be described later.

A time constant circuit 2 comprises a CR differentiator functioning as a filter which filters out DC components of an electrocardiogram waveform output from the differential amplifier 1. The time constant circuit 2 comprises a capacitor 2a and a resistor 2b which produce a CR time constant necessary for obtaining an appropriate electrocardiogram waveform. In this embodiment, the capacitor 2a has a capacity of 1 $\mu$F, the resistor 2b has a resistance value of 3.3 M$\Omega$, and, hence, the CR time constant is 3.3 seconds. An analog switch 2c connected in series with a resistor 2d is switched on/off depending on a switch signal SC1 from CPU 7.

Thus, when the analog switch 2c is switched on with the switch signal SC1 in the time constant circuit 2, the resistor 2d is connected in parallel with the resistor 2b to reduce the CR time constant of the time constant circuit 2. In the present embodiment, the resistor 2d has a resistance value of 330 K$\Omega$. When the analog switch 2c is switched on, the CR time constant becomes 0.3 seconds. What such arrangement is intended to provide will be described later.

An instruction switch 3 is switched on/off depending on a switch signal SC2 fed from CPU 7. The instruction switch 3 is switched on when the electrocardiogram waveform goes out of a set range of scales during recording to return the baseline level to the ground level.

An amplifier 4 appropriately amplifies the electrocardiogram waveform from the time constant circuit 2 and outputs the resulting signal to an A/D converter which performs an A/D conversion on the output from the amplifier 4.

When a measurement switch 6 is switched on, CPU 7 is instructed to start to perform a required measurement. CPU 7 includes a one-tip type microcomputer which contains a ROM 101 and a RAM 102. ROM 101 contains a control program for performing a waveform data measuring process of FIG. 3, etc. On the basis of this program, CPU 7 stores, for example, in an external RAM 8, cardiogram waveform data output from A/D converter 5, and also generates the sensitivity control signal S, switch signals SC1 and SC2 depending on the value of the cardiogram waveform data.

CPU 7 also generates a tone signal which includes the measured electrocardiogram waveform data modulated in an FSK system. The tone signal is amplified by a later stage amplifier 9 and outputted from a speaker 10.

If the tone signal outputted from the speaker 10 is sent, for example, through a telephone set to medical facilities such as hospitals, and such facilities demodulate and recording such tone signal, remote treatment and/or in-home medical examination/treatment using the electrocardiogram can be performed. Alternatively, in place of outputting the tone signal from the speaker 10 in the form of an audio output, the tone signal which includes electrocardiogram data modulated in the FSK system may be outputted directly to a telephone line. In this case, a modem is required to be provided which controls communication under the control of CPU 7, in place of the amplifier 9 and speaker 10.

B. Operation According to a First Embodiment

The operation according to the first embodiment will be described next. The user first sets the pair of electrodes T1 and T2 at required positions on the patient's body, turns on a power supply (not shown) of the portable electrocardiograph of this embodiment and switches on the measurement switch 6. In response to this operation, CPU 7 sequentially performs the following processes in accordance with the control program contained in ROM 101. CPU 7 regards the sensitivity setting period as having started since the switch 6 was switched on, generates a sensitivity control signal S which specifies a default amplification factor to first set a minimum amplification factor initially, and feeds it to the differential amplifier 1.

The differential amplifier 1 outputs an electrocardiogram waveform corresponding to a voltage across the electrodes T1 and T2 in an amplification factor depending on the sensitivity control signal S. DC components of the electrocardiogram waveform outputted from the differential amplifier 1 are cut when the electrocardiogram waveform passes through the time constant circuit 2 having the CR constant of 3.3 seconds, and the resulting signal is amplified appropriately, subjected to A/D conversion, and inputted as electrocardiogram waveform data into CPU 1.

Figure 2A:
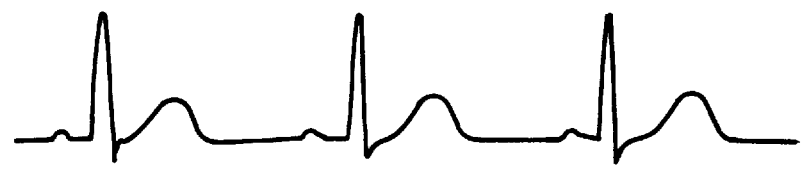
FIG. 2A is a waveform diagram illustrating the embodiments 1, 2 and a conventional example.

As shown in FIG. 2A, if the electrocardiogram waveform data has an appropriate waveform, normally, of about 1–2 millivolts, or, if the difference between the maximum and minimum peak values of the waveform is within a predetermined range, CPU 7 determines that the sensitivity is appropriate and stores the electrocardiogram waveform data sequentially into the external RAM 8.

Figure 2B:
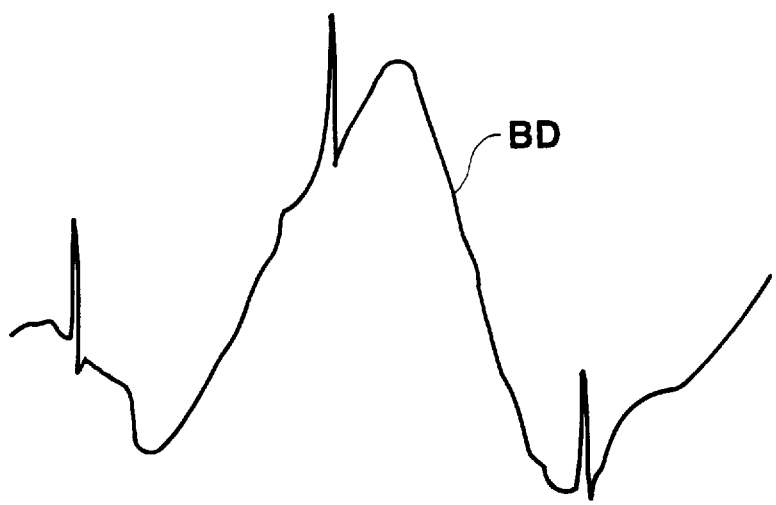
FIG. 2B is a waveform diagram illustrating the embodiments 1, 2 and a conventional example.

As shown in FIG. 2B, when the electrocardiogram waveform contains a superlow-frequency reference fluctuation BD, usually, of several times the voltage of the electrocardiogram waveform, the 3.3-second CR time constant circuit 2 cannot cut the superlow frequency components. Thus, the superlow frequency is directly amplified, subjected to A/D conversion and inputted as the electrocardiogram waveform data into CPU 7.

In this case, CPU 7 detects that the difference between the maximum and minimum peak values of the waveform is out of the predetermined range. In response to this operation, CPU 7 generates a switch signal SC1 to switch on the analog switch 2c to thereby eliminate the superlow frequency components which would otherwise cause the baseline fluctuation BD.

Figure 2C:
FIG. 2C is a waveform diagram illustrating the embodiments 1, 2.

When the analog switch 2c is turned on, the resistors 2d and 2b are connected in parallel. Thus, the CR time constant of the time constant circuit 2 is reduced, so that as shown in FIG. 2C, the time constant circuit 2 outputs an electrocardiogram waveform free from the superlow frequency components which would otherwise cause the baseline fluctuation BD.

CPU 7 then generates an amplification control signal S on the basis of the electrocardiogram waveform data free from the baseline fluctuation BD and feeds it to the differential amplifier 1 to set an appropriate sensitivity such that the difference between the maximum and minimum peak values of the waveform falls within a predetermined range.

A predetermined time after the appropriate sensitivity is set, CPU 7 outputs a switch signal SC1 which switches off the analog switch 2c to return the CR time constant of the time constant circuit 2 to the original value of 3.3 seconds.

At this time, if the contact of the electrodes T1 and T2 with the patient's skin is electrically stable and the baseline fluctuation BD has been settled, the amplification factor of the differential amplifier 1 is set at a sensitivity to provide an appropriate waveform level. Thus, an appropriate electrocardiogram waveform which can be used immediately for diagnosing purposes can be recorded.

When the contact between the electrodes T1, T2 and the patient's skin is not electrically stable and the baseline fluctuation BD is not settled even after the predetermined time has elapsed, the electrocardiogram waveform would go out of a set range of scales when the analog switch 2c is switched off. In this case, CPU 7 generates a switch signal SC2 which switches on the instruction switch 3, returns the baseline level of the electrocardiogram waveform to the ground level, and sets the sensitivity again.

As described above, in the first embodiment, when superlow frequency components (noise) which would cause a baseline fluctuation BD are superimposed on the electrocardiogram waveform, the CR time constant of the time constant circuit 2 is reduced such that the time constant circuit 2 acts as a bypass filter to eliminate the baseline fluctuation BD from the electrocardiogram waveform, and a sensitivity is set so as to ensure an optimal dynamic range. Thereafter, if the baseline fluctuation BD is settled, an appropriate cardiogram waveform used for the diagnosis is recorded immediately in the optimal dynamic range.

C. Operation According to the Second Embodiment

The operation according to the second embodiment will next be described with reference to a flow chart of FIG. 3. While in the first embodiment the analog switch 2C is switched on to reduce the CR time constant with the resistor 2d when a signal of FIG. 2B is detected at the beginning of the measurement, the analog switch 2C is always switched on at the beginning of the measurement where an unstable state is likely to occur to forcibly reduce the time constant with the resistor 2d, in the second embodiment.

The user first sets the pair of electrodes T1 and T2 at required positions on the patient's body, turns on the power supply (not shown) of the portable electrocardiograph of this embodiment and switches on the measurement switch 6. In response to this operation, CPU 7 sequentially performs the following processes in accordance with the control program contained in ROM 101. More particularly, CPU 7 regards the sensitivity setting period as having started since the switch 6 was switched on (step S1), and generates a sensitivity control signal S which specifies a default amplification factor to set a minimum amplification factor initially, and feeds it to the differential amplifier 1 (step S2).

CPU 7 then generates a switch signal SC1 to switch on the analog switch 2c to thereby eliminate the superlow frequency components which would otherwise cause the baseline fluctuation BD first (step S3).

When the analog switch 2c is switched on, the CR time constant of the time constant circuit 2 is reduced because the resistors 2d and 2b are connected in parallel. Thus, even when the electrocardiogram waveform outputted from the differential amplifier 1 takes the form of FIG. 2A which has a level of 1–2 millivolts or FIG. 2B which is several to scores of the signal level of FIG. 2A, the time constant circuit 2 outputs an electrocardiogram waveform of FIG. 2C which has substantially the same level as that of FIG. 2A.

The outputted electrocardiogram waveform is then amplified by the amplifier 4 and subjected to the A/D conversion by the A/D converter, and the resulting signal is inputted to CPU 7.

At step S4, CPU 7 detects the minimum and maximum peak values of the inputted electrocardiogram waveform to obtain its amplitude from the electrocardiogram waveform.

At step S5, CPU 7 obtains an appropriate sensitivity for the measurement of the current electrocardiogram waveform such that the difference (amplitude) between the minimum and maximum peak values of the electrocardiogram waveform detected at step S4 falls within the predetermined range.

In the processing at steps S4 and S5, the minimum and maximum peak values of the electrocardiogram waveform are required to be obtained through at least one period of the electrocardiogram waveform. Thus, at step SB, the processing at steps 4 and 5 is repeated until a predetermined time (2 seconds) elapses.

When CPU 7 determines at step S6 that the predetermined time (2 seconds) has elapsed, the control passes to step S7, where CPU 7 generates a sensitivity control signal S which controls the amplification factor of the differential amplifier 1 depending on the sensitivity obtained at step S5, and sets the amplification factor of the differential amplifier 1 so as to provide an appropriate sensitivity for the measurement of the electrocardiogram waveform to be made this time.

Thereafter, at step S8, CPU 7 outputs a switch signal SC1 which switches off the analog switch 2c to return the CR time constant of the time constant circuit 2 to the original value of 3.3 seconds.

At this time, if the contact of the electrodes T1 and T2 with the patient's skin is electrically stable and the baseline fluctuation BD has been settled, the amplification factor (or sensitivity) of the differential amplifier 1 has been set to provide an appropriate waveform level. Thus, an appropriate electrocardiogram waveform which can be used immediately for diagnosis can be recorded.

When the contact between the electrodes T1, T2 and the patient's skin is not electrically stable and the baseline fluctuation BD is not settled even after the predetermined time has elapsed, the electrocardiogram waveform would go out of the set range of scales when the analog switch 2c is switched off. In this case, CPU 7 generates a switch signal SC2 which switches off the instruction switch 3, returns the baseline level of the electrocardiogram waveform to the ground level, and sets the sensitivity again at steps S2–S6.

As set forth hereinabove, the embodiments 1 and 2, have been described as handling analog signals up to the input stage of the A/D converter 5. Alternatively, in an arrangement where the output of the differential amplifier 1 is directly A/D converted to a digital signal and this digital signal is handled, the time constant circuit 2 may be replaced with a digital one whose coefficient is controlled by CPU 7 to filter out noise. In this case, as the digital filter, a notch filter having a plurality of bandwidths which eliminates superlow frequency components which would cause a baseline fluctuation BD, and a power source hum and its harmonic components is effective. The notch filter may be realized by either hardware or software executed by CPU 7.

What is claimed is:

1. A sensitivity setting device for setting an optimal measurement sensitivity in an electrocardiograph, said sensitivity setting device comprising:

measurement starting means for starting a measurement of an electrocardiogram waveform inputted to the electrocardiograph;

an amplifier which amplifies the electrocardiogram waveform at a given amplification factor;

a filter which filters possible noise out from the electrocardiogram waveform with a predetermined time constant;

time constant setting means for setting the time constant of said filter at a value smaller than the predetermined time constant only for a predetermined given period of time immediately after said measurement starting means starts the measurement of the electrocardiogram waveform;

an amplitude detector which detects an amplitude of the filtered electrocardiogram waveform in accordance with the smaller time constant set by said time constant setting means for the predetermined given period of time immediately after said measurement starting means starts the measurement of the electrocardiogram waveform; and amplification factor setting means for setting the given amplification factor of said amplifier at a value such that the amplitude detected by said amplitude detector falls within a predetermined range.

2. The sensitivity setting device according to claim 1, wherein:

said sensitivity setting device is provided in a portable electrocardiograph; and said measurement starting means comprises key-in means operable by a user for instructing the electrocardiograph to start the measurement of the electrocardiograph waveform.

3. The sensitivity setting device according to claim 1, wherein:

said filter comprises a capacitor and a resistor; and said time constant setting means comprises a resistor connection which connects another resistor with said filter for setting the time constant of said filter at, the value smaller than the predetermined time constant only for the Predetermined given period of time immediately after said measurement starting means starts the measurement of the electrocardiogram waveform.

4. The sensitivity setting device according to claim 1, further comprising stop means for stopping input of the electrocardiograph waveform to the electrocardiograph when the amplitude of the electrocardiogram waveform detected by said amplitude detector is out of the predetermined range at the amplification factor set by said amplification factor setting means.

5. The sensitivity setting device according to claim 1, wherein said time constant setting means comprises:

initial amplitude determining means for determining whether an initial amplitude of the inputted electrocardiogram waveform is within the predetermined range after said measurement starting means has started the measurement of the electrocardiogram waveform; and initial time constant setting means for setting the time constant of said filter at the value smaller than the predetermined time constant for the predetermined given period of time only when said initial amplitude determining means determines that the initial amplitude of the inputted electrocardiogram waveform is not within the predetermined range.

6. A recording medium containing a computer readable program for controlling a computer to function as:

measurement starting means for starting a measurement of an electrocardiogram waveform;

amplifying means for amplifying the electrocardiogram waveform at a given amplification factor;

filter means for filtering possible noise out from the electrocardiogram waveform with a predetermined time constant;

time constant setting means for setting the time constant of said filter means at a value smaller than the predetermined time constant only for a given period of time after said measurement starting means starts the measurement of the electrocardiogram waveform;

amplitude detecting means for detecting an amplitude of the filtered electrocardiogram waveform in accordance with the time constant set by said time constant setting means; and amplification factor setting means for setting the given amplification factor of said amplifier at a value such that the amplitude detected by said amplitude detecting means falls within a predetermined range.

7. A method of optimally setting a measurement sensitivity of an electrocardiograph comprising the steps of:

starting a measurement of an electrocardiogram waveform inputted to the electrocardiograph;

amplifying the electrocardiogram waveform at a given amplification factor;

filtering possible noise out from the electrocardiogram waveform using a filter having a predetermined time constant;

setting the time constant of said filter at a value smaller than the predetermined time constant only for a predetermined given period of time immediately after said step of starting the measurement of the electrocardiogram waveform;

detecting an amplitude of the filtered electrocardiogram waveform in accordance with the time constant set at the value smaller than the predetermined time constant for the predetermined period of given time immediately after said step of starting the measurement of the electrocardiogram waveform; and setting the given amplification factor at a value such that the detected amplitude falls within a predetermined range.

* * * * *